United States Patent
Thorley et al.

(10) Patent No.: US 9,352,104 B2
(45) Date of Patent: May 31, 2016

(54) SYRINGE BARREL ADAPTER AND NEEDLE ASSEMBLY

(75) Inventors: Craig Stephen Thorley, Largs (AU); Joseph Hermes Kaal, Raworth (AU); Christopher Charles Rafferty, Raworth (AU)

(73) Assignee: Unitract Syringe PTY LTD, Sydney (AU)

( * ) Notice: Subject to any disclaimer, the term of this patent is extended or adjusted under 35 U.S.C. 154(b) by 583 days.

(21) Appl. No.: 13/695,599

(22) PCT Filed: May 4, 2011

(86) PCT No.: PCT/AU2011/000515
§ 371 (c)(1),
(2), (4) Date: Dec. 28, 2012

(87) PCT Pub. No.: WO2011/137488
PCT Pub. Date: Nov. 10, 2011

(65) Prior Publication Data
US 2013/0102973 A1    Apr. 25, 2013

Related U.S. Application Data

(60) Provisional application No. 61/331,197, filed on May 4, 2010.

(51) Int. Cl.
*A61M 5/34*    (2006.01)
*A61M 5/50*    (2006.01)
*A61M 39/10*   (2006.01)

(52) U.S. Cl.
CPC ............. *A61M 5/34* (2013.01); *A61M 5/344* (2013.01); *A61M 5/50* (2013.01); *A61M 5/345* (2013.01); *A61M 5/346* (2013.01); *A61M 2039/1077* (2013.01)

(58) Field of Classification Search
CPC .......... A61M 5/34; A61M 5/344; A61M 5/50; A61M 2039/1077; A61M 5/345; A61M 5/346
See application file for complete search history.

(56) References Cited

U.S. PATENT DOCUMENTS 5,125,899 A    6/1992   Frignoli
5,211,629 A *  5/1993   Pressly ............... A61M 5/3234
                                                              604/110

(Continued)

FOREIGN PATENT DOCUMENTS

CA    2504446 A1    3/2006
CN    2836824 A     11/2006

(Continued)

OTHER PUBLICATIONS

Australian Patent Office, International Search Report in International Patent Application No. PCT/AU2011/000515 (Aug. 11, 2011).

(Continued)

*Primary Examiner* — Bhisma Mehta
*Assistant Examiner* — Bradley Osinski
(74) *Attorney, Agent, or Firm* — Leydig, Voit & Mayer, Ltd.

(57) ABSTRACT

An adapter mountable to a retractable syringe barrel comprises a body that includes a needle portion and a barrel-engaging portion and a needle aperture. The adapter facilitates mounting a needle assembly to the barrel. The needle assembly comprises a needle body and cannula and an immobile, compressible needle seal, wherein the needle body and the needle seal are releasably engaged. The needle seal is engageable with a needle portion of the adapter. The needle body comprises one or more fluid reclaim channels that facilitate efficient delivery of the fluid contents of the retractable syringe. The retractable syringe also comprises dual locking systems to impede or prevent re-use.

13 Claims, 15 Drawing Sheets

(56) References Cited

U.S. PATENT DOCUMENTS

| | | | |
|---|---|---|---|
| 5,395,337 A * | 3/1995 | Clemens et al. | 604/110 |
| 5,417,661 A | 5/1995 | Stringer et al. | |
| 5,520,649 A | 5/1996 | Novacek et al. | |
| 5,876,382 A | 3/1999 | Erickson | |
| 2002/0111588 A1 * | 8/2002 | Restelli | A61M 5/3234 604/218 |
| 2003/0229314 A1 | 12/2003 | McWethy et al. | |
| 2005/0096604 A1 | 5/2005 | Maggioni | |
| 2005/0159705 A1 | 7/2005 | Crawford et al. | |

FOREIGN PATENT DOCUMENTS

| | | |
|---|---|---|
| EP | 1625865 B1 | 3/2009 |
| TW | 200610553 A | 3/2006 |
| WO | WO 2008-136775 A2 | 11/2008 |
| WO | WO 2009-003234 A1 | 1/2009 |

OTHER PUBLICATIONS

Australian Patent Office, Written Opinion in International Patent Application No. PCT/AU2011/000515 (Aug. 11, 2011).

Australian Patent Office, International Preliminary Report on Patentability in International Patent Application No. PCT/AU2011/000515 (Feb. 14, 2012).

European Patent Office Extended European Search Report, including supplementary European search report and the European search opinion, Oct. 24, 2014 (6 pages).

Taiwan Intellectual Property Office, Examination Report from the Intellectual Property Office, Jul. 17, 2014, 16 pgs., Taiwan.

* cited by examiner

SYRINGE BARREL ADAPTER AND NEEDLE ASSEMBLY

CROSS-REFERENCE TO RELATED APPLICATIONS

This patent application is the U.S. national phase of International Patent Application No. PCT/AU2011/000515 filed May 4, 2011, which claims the benefit of U.S. Provisional Patent Application No. 61/331,197, filed May 4, 2010, which are incorporated by reference in their entireties herein.

FIELD

THIS INVENTION relates to syringes. More particularly, this invention relates to an adapter and/or a needle assembly mountable to a retractable syringe barrel and/or a retractable syringe comprising same.

BACKGROUND

The practice of sharing syringes without adequate sterilization between successive users is a major contributor to the transfer of Human Immunodeficiency Virus (HIV) and Hepatitis with subsequent severe repercussions for the sufferer and at a high cost to society for supporting and providing medical attention to sufferers.

Furthermore, health professionals may be exposed to used syringes which can lead to inadvertent needlestick injuries and possible exposure to infective pathogens or other contaminants.

In response to this problem, retractable syringes have been developed with the aim of preventing syringe re-use and/or needlestick injury by used syringes.

In developing such retractable syringes, relatively complicated retractable needle assemblies have been devised which often are adapted for a particular syringe barrel shape or configuration and cannot be readily mounted to a syringe barrel having a different shape or configuration. This is particularly a problem with glass syringe barrels which are generally in short supply, many of which glass barrels do not have a desired shape or configuration for mounting a retractable needle assembly.

SUMMARY

An object of the invention is to provide an adapter which facilitates mounting of a needle assembly to a retractable syringe. A preferred object of the invention is to provide an adapter which obviates the need to have a particular barrel shape or configuration for mounting a needle assembly thereto. Another preferred object of the invention is to provide a relatively simplified needle assembly which comprises fewer components, thereby providing a user friendly and safe retractable syringe while keeping manufacturing costs to a minimum and/or facilitating mass distribution of retractable syringes. In other, preferred objects the invention is to provide efficiently delivery of fluid contents, thereby minimizing wastage of fluid contents and/or one or more locking systems to prevent or at least minimize syringe re-use and/or needle stick injury.

In a first aspect, the invention provides an adapter mountable to a syringe barrel, said adapter comprising a body that includes a needle portion and a barrel-engaging portion.

Suitably, said adapter is capable of coupling or mounting to, or engaging with, a needle assembly of said retractable syringe.

Preferably, the adapter further comprises a needle aperture. Suitably, when the adapter is coupled with the needle assembly, a cannula of the needle assembly is received or accommodated by, or extends through, the needle aperture of the adapter.

In a second aspect, the invention provides a needle assembly mountable to a syringe barrel adapter, said needle assembly comprising a needle body and cannula and a needle seal, wherein the needle body and needle seal are releasably engaged.

Suitably, the needle assembly is capable of coupling or mounting to, or engaging with a retractable syringe barrel adapter comprising a body that includes a needle portion and a barrel-engaging portion.

Preferably, in use the needle seal is compressible.

Preferably, in use the needle seal is substantially immobile.

In a particularly preferred embodiment, the needle seal is engageable with a needle portion of said adapter.

Preferably, the needle body comprises one or more fluid reclaim channels. In one form, the fluid reclaim channels are two opposed channels operable to direct fluid into said cannula.

In a third aspect, the invention provides a syringe barrel comprising the adapter of the first aspect and the needle assembly of the second aspect.

In a fourth aspect, the invention provides a syringe comprising the adapter of the first aspect, the needle assembly of the second aspect or the syringe barrel of the third aspect and a plunger.

Preferably, the plunger comprises a plunger outer and a plunger member.

Preferably, the plunger further comprises a biasing member.

Suitably, retraction of said retractable needle is facilitated by said biasing member.

Non-limiting examples of biasing members include a spring, elastic or other device for storing releasable energy. Preferably, the biasing member is a spring.

Preferably, the plunger member and plunger outer co-operate to releasably maintain said biasing member in an initially energized state.

In one embodiment, the plunger further comprises a retractable needle-engaging member.

Preferably, the plunger further comprises a plunger seal.

In one embodiment, the plunger seal is mounted to the plunger member.

In one preferred embodiment, the plunger seal comprises said retractable needle-engaging member.

Preferably, the needle-engaging member is capable of engaging said needle body to facilitate needle retraction.

The plunger may further comprise a controlling member to facilitate control of the rate of retraction. Preferably, the control rod is releasably connected to the plunger member. In a particular form, the control rod is frangibly connected to the plunger member.

Preferably, said controlling member is releasably coupled to said outer member to maintain said biasing means in an initially energized state. More preferably, said barrel further comprises a collar having one or more releasing members that facilitate release of said controlling member from said plunger outer member.

It will be appreciated that the invention contemplates particular embodiments of said plunger. Preferably, according to these embodiments the plunger comprises one or more elements that facilitate locking the plunger to the barrel after injection of fluid contents of said syringe and/or after needle retraction is complete to prevent or impede re-use of the syringe.

In one embodiment, the plunger comprises a plunger member, a plunger outer and a first locking member that prevents or impedes further movement of said plunger member relative to said plunger outer and/or said barrel after needle retraction. Suitably, the locking member is mounted to the plunger outer. In a particular embodiment, the locking member is a lock spring.

According to this embodiment, preferably, there is further provided another lock formed between elements of the barrel, or collar mounted to the barrel, and the plunger outer after injection of fluid contents of said syringe. Preferably, the plunger outer comprises a second locking member which is capable of engaging the barrel. Suitably, the second locking member is capable of engaging the barrel at the end of injection of fluid contents to thereby prevent or impede further movement of the plunger outer relative to the barrel.

An example of such a preferred embodiment is provided in PCT/AU2010/001677, which is incorporated herein by reference.

In an alternative embodiment, one said locking system comprises respective elements of said barrel and said plunger outer. Preferably, according to this embodiment the locking system comprises elements of said collar and said plunger outer.

In another form of this alternative embodiment, another said locking system comprises elements of said plunger member and said plunger outer.

Preferably, said syringe comprises both said locking systems.

Examples of locking systems according to this alternative embodiment are described in International Publication WO2009/003234, which is incorporated herein by reference.

In a fifth aspect, the invention provides a method of assembly of the needle assembly of the second aspect, the syringe barrel of the third aspect and/or the syringe of the fourth aspect, which includes the step of assembling components thereof to thereby produce the needle assembly of the second aspect, the syringe barrel of the third aspect and/or the syringe of the fourth aspect.

In a sixth aspect, the invention provides a method of use of the syringe of the fourth aspect which includes the step of delivering fluid contents of the syringe to a human.

Preferably, the syringe of the aforementioned aspects is a retractable syringe.

More preferably, the syringe is a pre-filled retractable syringe.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the following drawings wherein.

DETAILED DESCRIPTION

Figure 1:
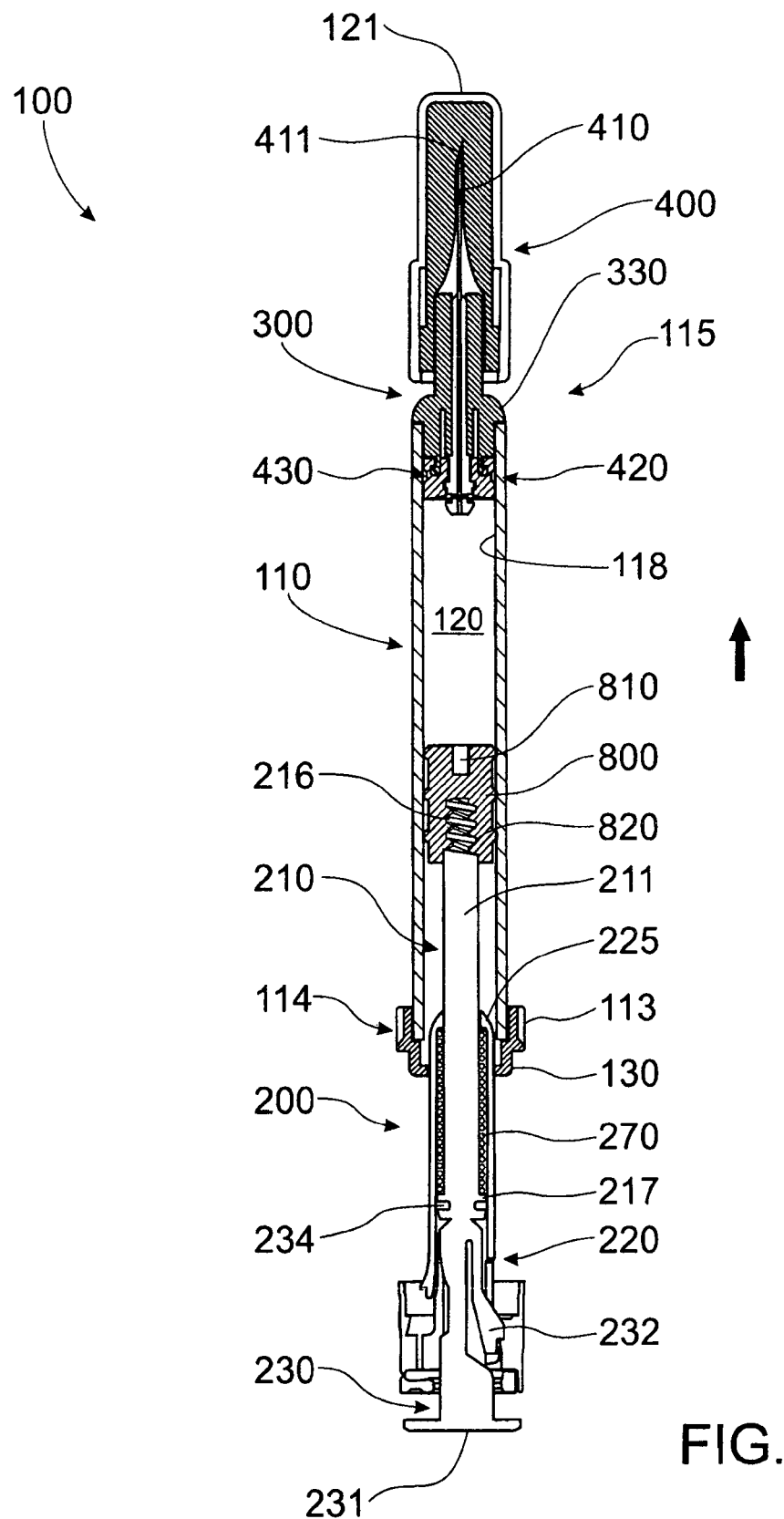
FIG. 1 is a sectional view of an embodiment of a retractable syringe.

Referring to FIG. 1, an embodiment of retractable syringe 100 comprises barrel 110 having plunger end 114 and needle end 115. Barrel 110 is substantially cylindrical in shape and is preferably formed of glass. At plunger end 114 of barrel 110 is located collar 113 having release ring 130. Collar 113 may be mounted, glued, fitted or integrally formed with barrel 110. In embodiments where barrel 110 is formed of glass, collar 113 is glued or otherwise adhered to barrel 110. In alternative embodiments where barrel 110 is formed of plastic or other mould-able material, collar 113 is formed integrally with barrel 110 (e.g by moulding). Release ring 130 may be mounted or otherwise fitted to barrel 110, or may be co-moulded with collar 113 and barrel 110. Typically, syringe 100 is supplied with protective cover 121 over cannula 410 to protect cannula tip 411. At needle end 115 of barrel 110 is mounted barrel adapter 300 and needle assembly 400 comprising cannula 410, needle body 420 and needle seal 430. Syringe 100 further comprises plunger 200 comprising plunger seal 800 mounted thereto. Barrel 110 further comprises inside wall 118 which, together with needle body 420, needle seal 430 and plunger seal 800 defines fluid space 120 inside barrel 110. As shown in FIG. 1, in use plunger 200 is movable axially into fluid space 120 in the direction of the solid arrow to facilitate delivery of fluid contents of retractable syringe 100. In a preferred embodiment, fluid space 120 is prefilled with fluid contents to be delivered by retractable syringe 100. In this context, by "prefilled" is meant that retractable syringe 100 is provided to the user filled with deliverable fluid contents without the need for the user to fill barrel 110 with the fluid contents.

Figure 2:
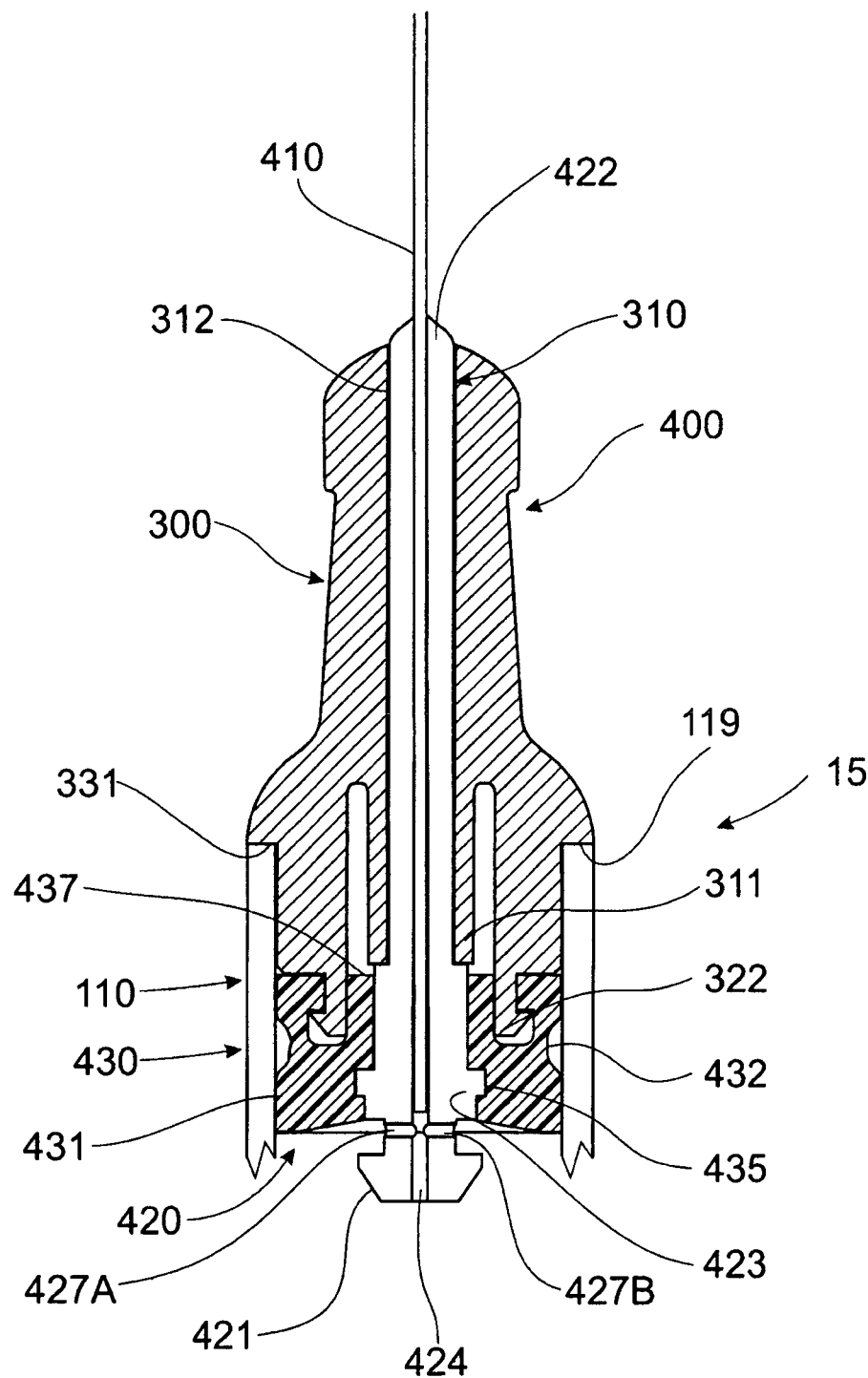
FIG. 2 is a sectional view of an embodiment of an adapter and needle assembly mounted to a retractable syringe barrel.
Figure 3:
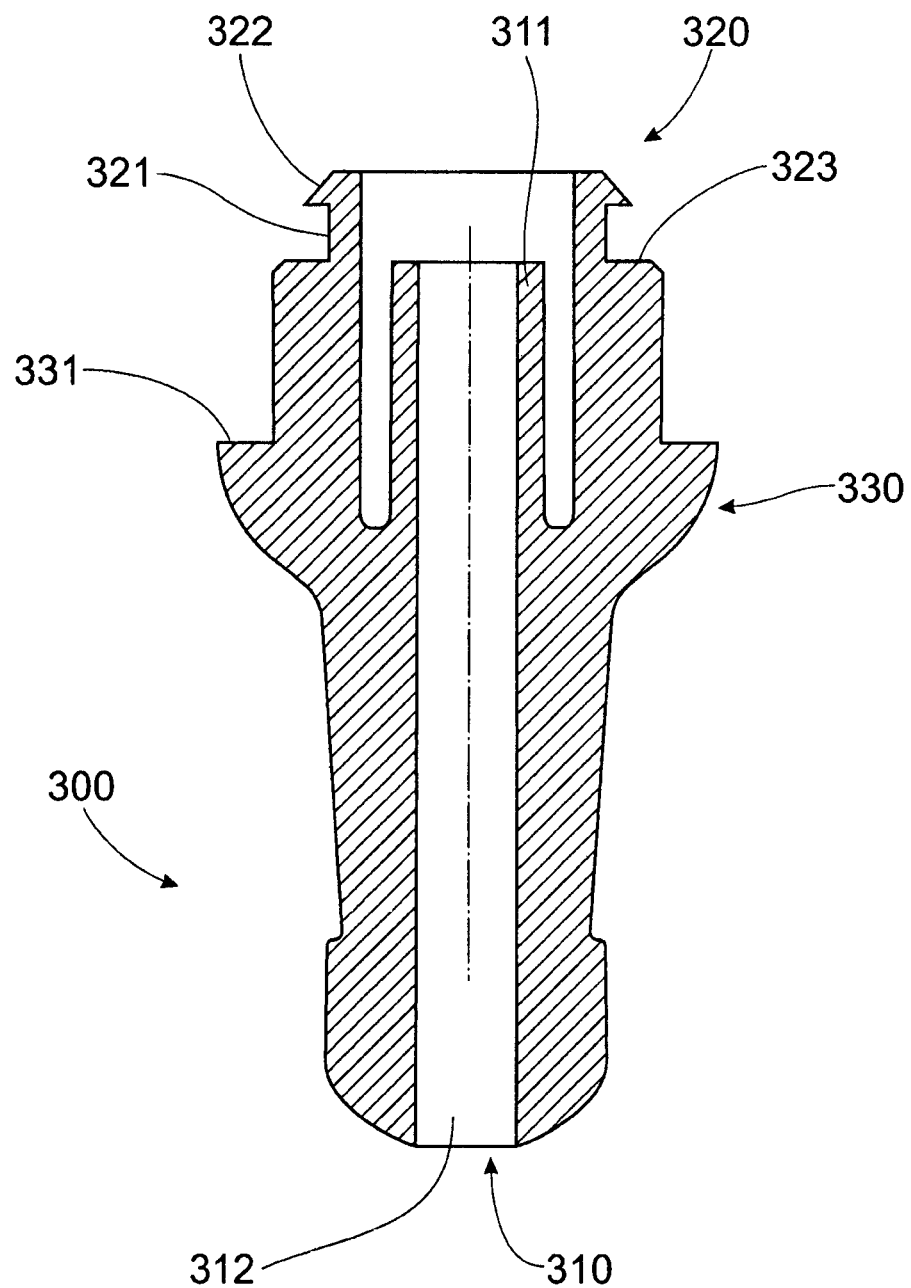
FIG. 3 is a sectional view of an embodiment of an adapter.
Figure 4:
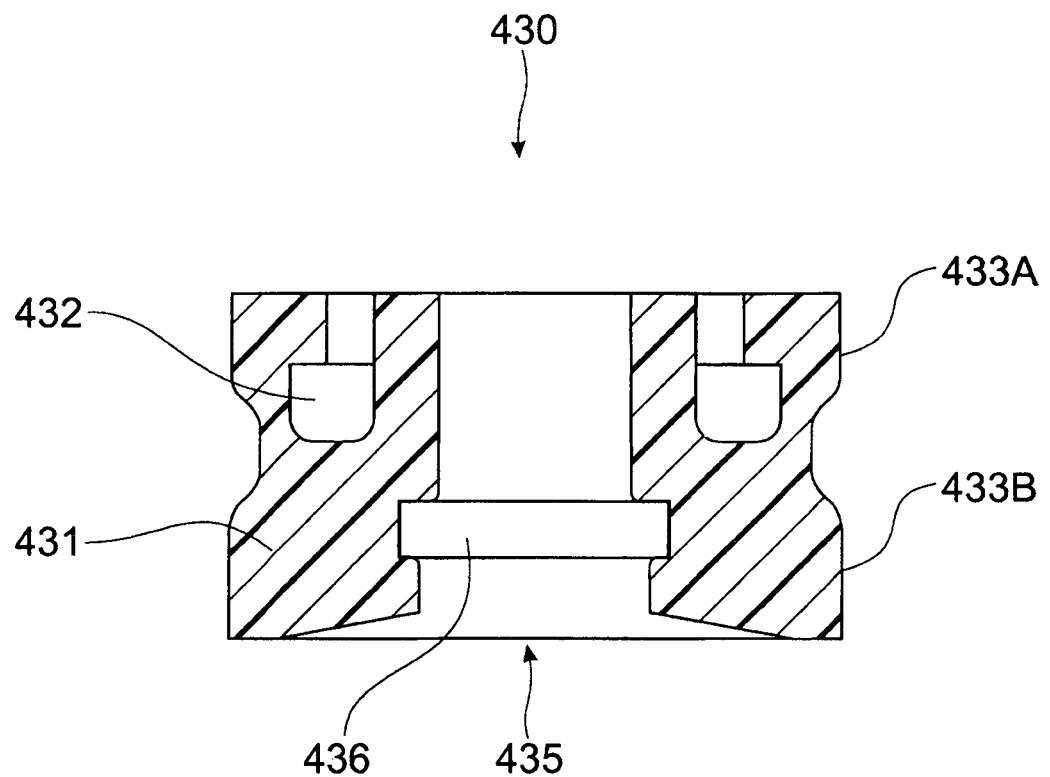
FIG. 4 is a sectional view of an embodiment of a needle seal.
Figure 5:
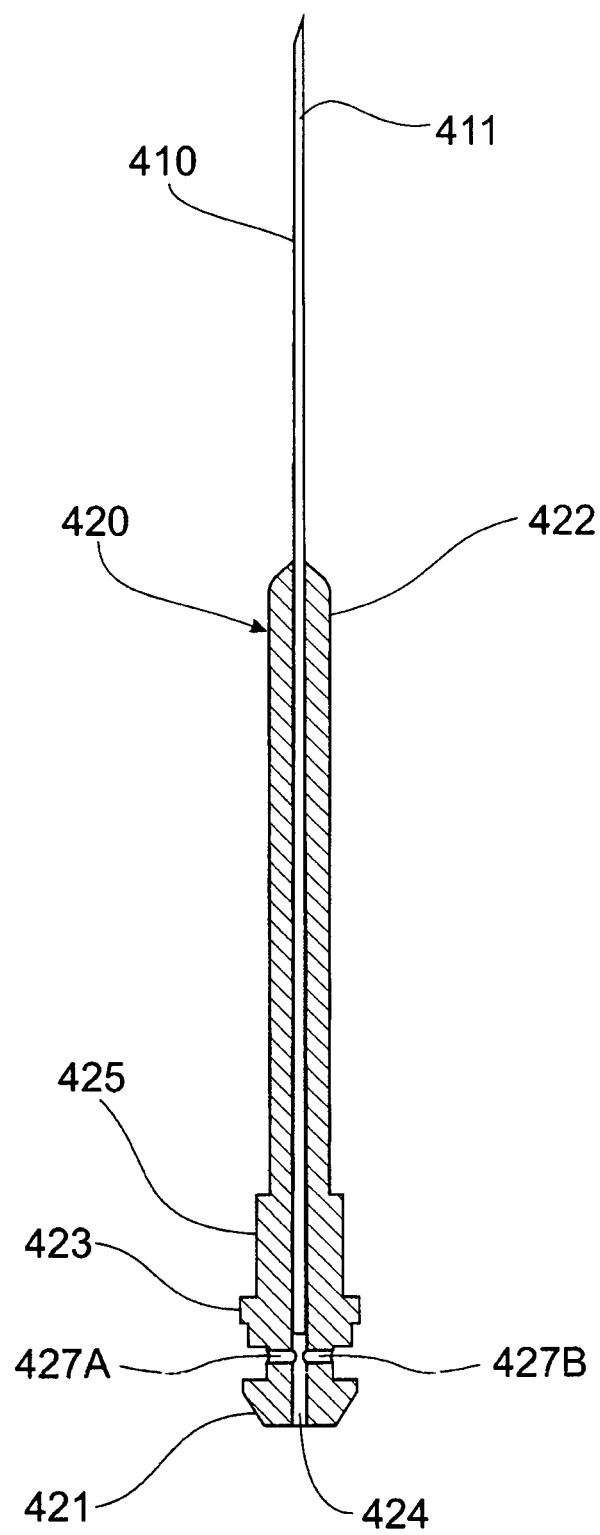
FIG. 5 is a sectional view of an embodiment of a needle body and cannula.

Referring to FIG. 2 and FIG. 3, barrel adapter 300 comprises needle portion 310 that comprises spigot 311 and needle aperture 312; needle seal-engaging member. 320 that comprises mounting ring 321 having annular barb 322 and shoulder 323; and barrel-engaging portion 330 that comprises circumferential shoulder 331 which bears against rim 119 of barrel 110. Referring to FIGS. 2 to 5, needle assembly 400 comprises, cannula 410 and needle body 420 comprising plunger-engaging member 421, elongate body 422 having retaining step 423, bore 424 and opposed fluid reclaim channels 427A,B in fluid communication with bore 424 and cannula 410, neck 425 and needle seal 430. Needle seal 430 comprises body 431 having barb seat 432 and sealing ribs 433A, 433B that facilitate a fluid seal against inside wall 118 of barrel 110. Needle seal 430 further comprises needle bore 435 having needle retaining portion 436 of increased diameter compared to the diameter of bore 435. As seen in FIG. 2, barb seat 432 accommodates annular barb 322 of mounting ring 321 of needle seal-engaging portion 320 of barrel adapter 300 to thereby couple needle seal 430 to barrel adapter 300. Spigot 311 bears against surface 437 of needle body 420 and cannula 410 extends through needle aperture 312 so that cannula tip 411 is free for delivery of fluid contents once cover 121 is removed. This arrangement renders needle seal 430 immobile at all stages of retractable syringe 100 use.

Figure 6:
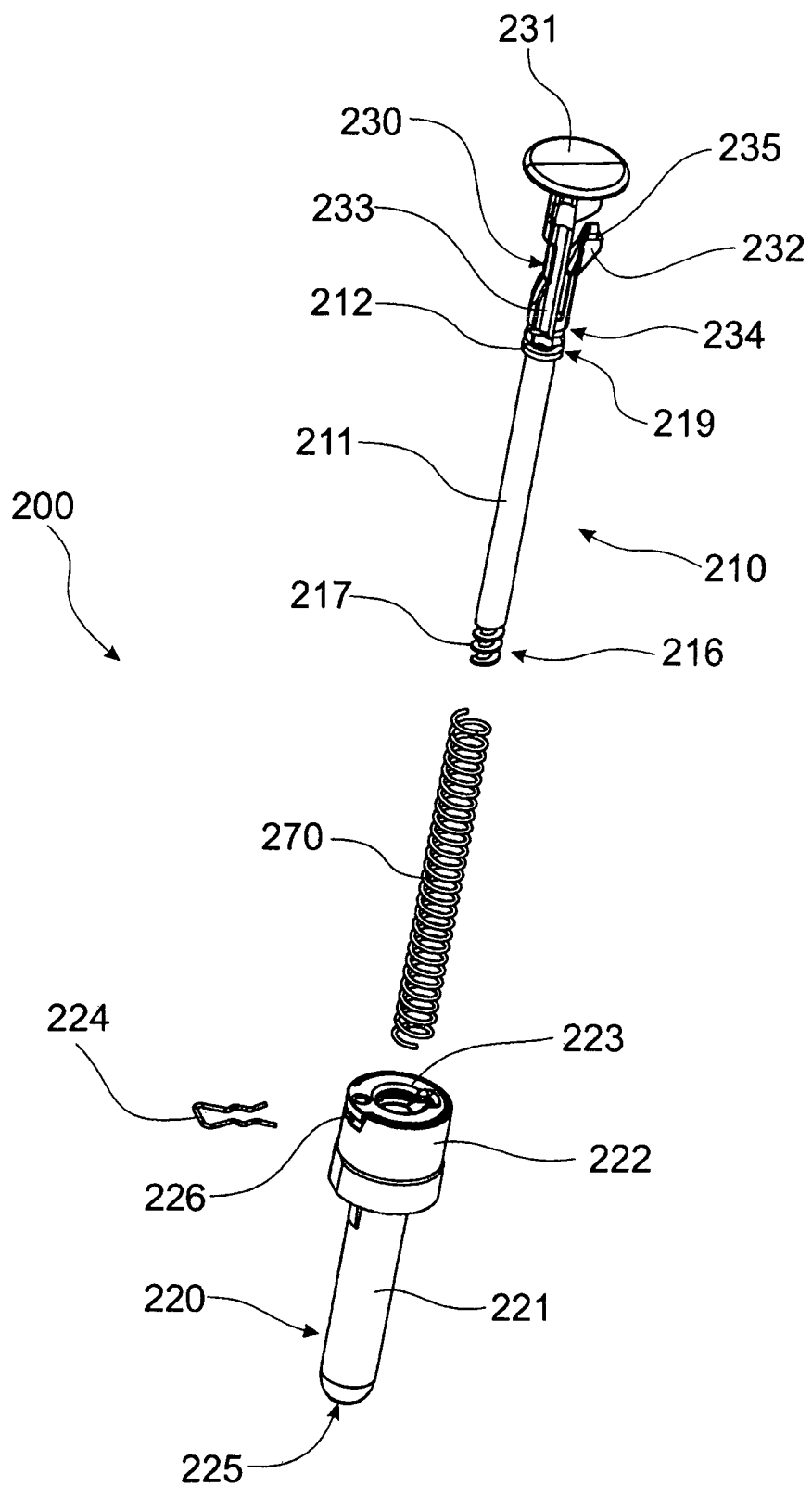
FIG. 6 is an exploded perspective view of an embodiment of a plunger.
Figure 7:
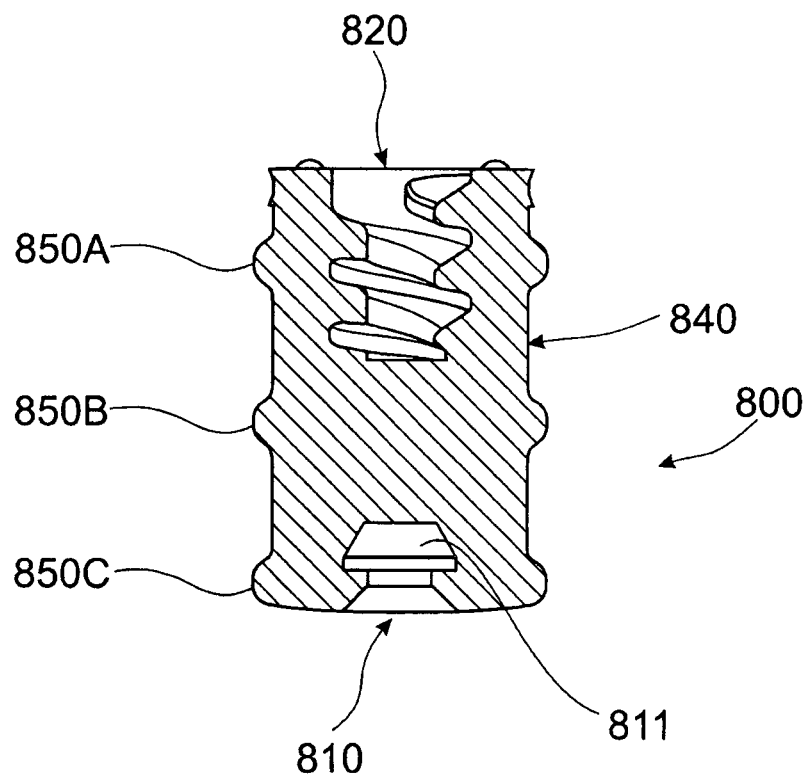
FIG. 7 is a sectional view of an embodiment of a plunger seal.

Referring particularly to FIG. 6 and FIG. 7, plunger 200 comprises plunger member 210 comprising shaft 211, annular ledge 212 and seal-engaging member 216, which in this embodiment is screw-threaded projection 217, which engages complementary recess 820 of plunger seal 800. In an alternative embodiment, seal-engaging member 216 may be in the form of a snap lock projection that engages a complementary recess in plunger seal 800. Referring particularly to FIG. 7, plunger seal 800 is of unitary construction and comprises seal body 840 and sealing ribs 850A, 850B, 850C that effect a fluid-tight seal between plunger 200 and inside wall 118 of barrel 110. Recess 820 of plunger seal 800 engages complementary seal-engaging member 216 of plunger member 210. In this embodiment, recess 820 comprises a female screw thread 821 that engages male screw-threaded projection 217 of plunger member. Plunger seal 800 further comprises needle-engaging member in the form of recessed seat 810 comprising flange 811 that can receive plunger-engaging member 421 of needle body 420.

Referring particularly to FIG. 6, plunger member 210 further comprises locking groove 219, the function of which will be described in more detail hereinafter.

Plunger 200 further comprises plunger outer 220 having elongate body 221 with base 225 and head 222 in which is fitted cap 223. A first locking member comprises lock spring 224 mounted through slot 226 extending through head 222 and cap 223 to thereby assist assembly of plunger 200. Typically, lock spring 224 is an "R-shape" clip of stainless steel construction. Lock spring 224 and locking groove 219 co-operate to lock plunger member 210 and plunger outer 220 together at the end of retraction, as will be described in more detail hereinafter with particular reference to FIG. 10. Lock spring 224 may provide up to 100 Newton "lockout" resistance, which is a level of resistance desirable for syringe 100.

Elongate body 221 further comprises a second locking member comprising locking finger 227 which has abutment 228. This also seen in FIG. 8. Engagement between locking finger 227 and release ring 130 of collar 113 will also be described in more detail hereinafter with particular reference to FIG. 10.

As shown in FIG. 6, releasably, frangibly engaged with plunger member 210 is control rod 230 comprising button 231, arm 232 and shaft 233. Plunger 200 further comprises compressed spring 270 which is mounted between plunger member 210 and plunger outer 220, held in an initially compressed state between annular ledge 212 of plunger member 210 and base 225 of plunger outer 220. Button 231 may have a textured surface to improve feel and grip for a user.

Figure 8:
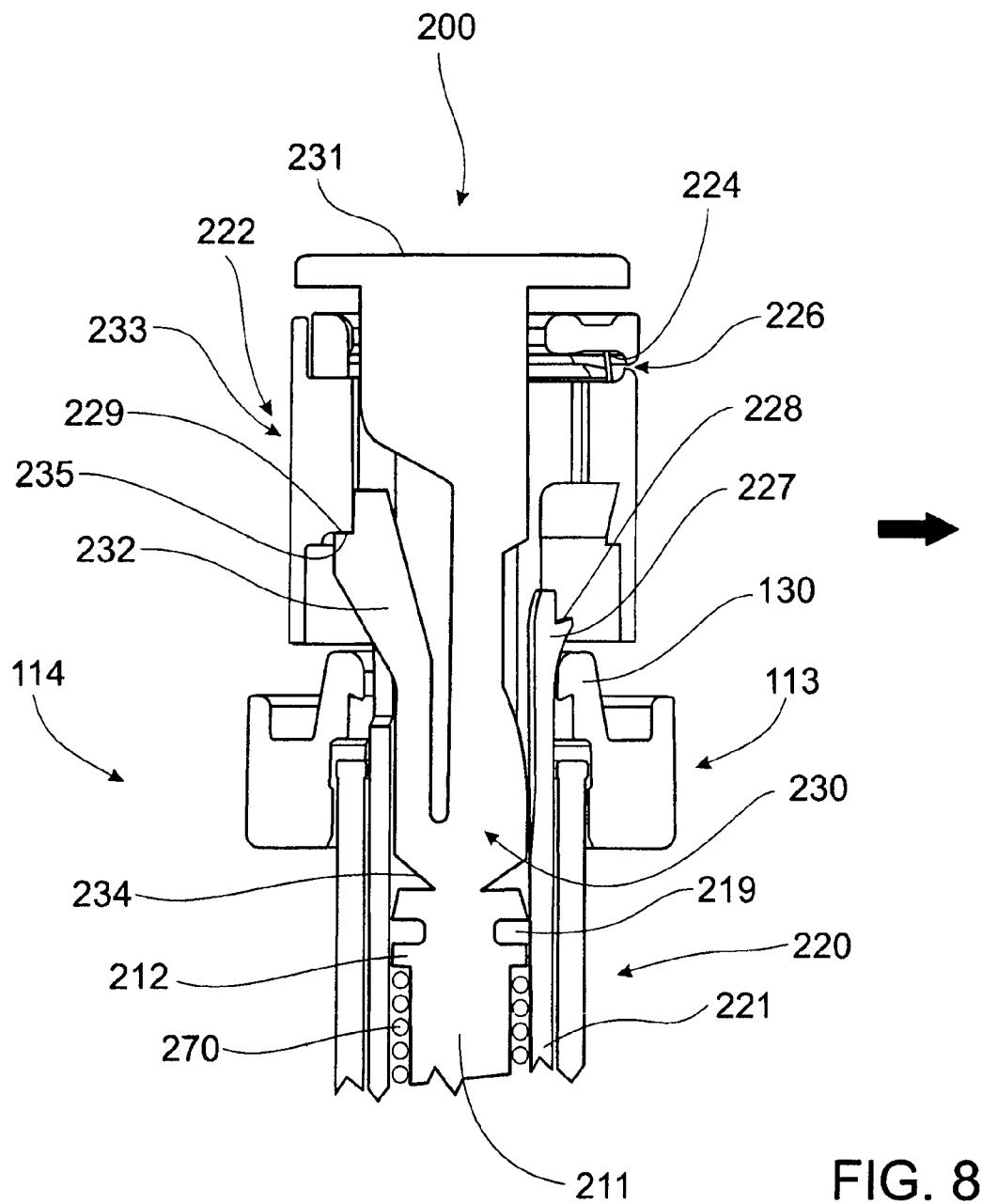
FIG. 8 is a sectional view of an embodiment of a plunger immediately before the end of injection of fluid contents of a retractable syringe.

As best shown in FIG. 8, control rod 230 is releasably coupled to plunger member 210 by way of shaft 233 which is releasably connected to plunger member 210 by frangible junction 234. Control rod 230 also releasably engages plunger outer 220 to thereby retain spring 270 in an initially compressed state held between annular ledge 212 of plunger member 210 and base 225 of plunger outer 220. Initially, ledge 235 of arm 232 abuts rim 229 of head 222 of plunger outer 220 to thereby retain control rod 230 and prevent axial movement of control rod 230 relative to plunger outer 220. However, arm 232 of control rod 230 is resiliently flexible and movable in the direction of the solid arrow shown in FIG. 8, which will allow disengagement of control rod 230 from plunger outer 220 to facilitate decompression of spring 270, as will be described in detail hereinafter.

The sequence of events whereby retractable needle 400 is disengaged from needle seal 430 to facilitate retraction of retractable needle 400 is as follows.

Figure 9:
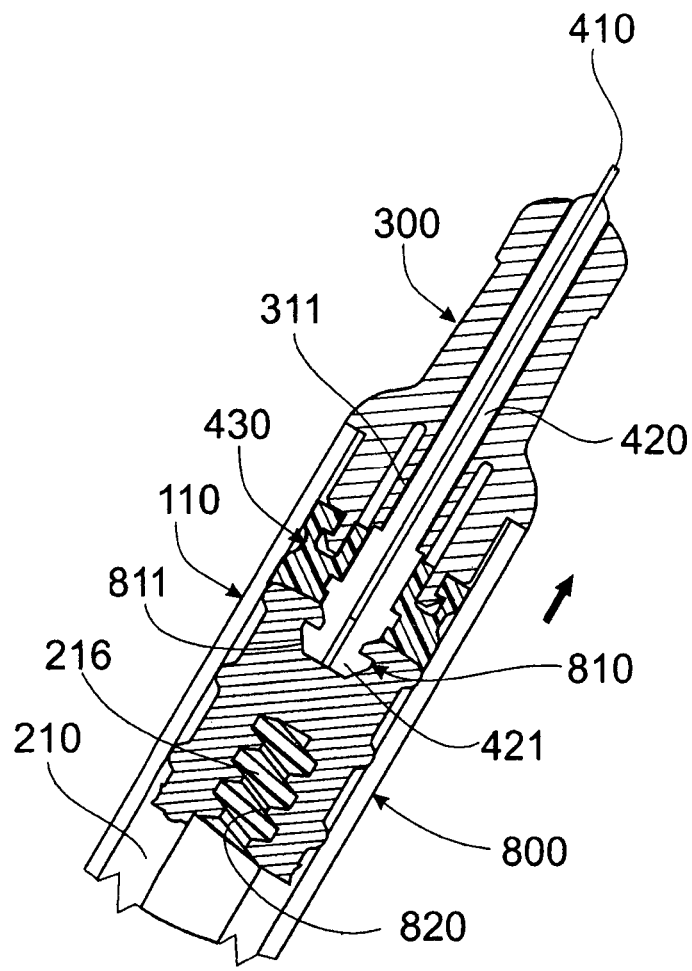
FIG. 9 is a sectional view of an embodiment of a needle body coupled to a plunger seal prior to needle retraction.

Typically, syringe 100 is provided prefilled with fluid contents for delivery. Therefore, plunger 200 is provided in an initial position ready for depression to deliver the fluid contents of the syringe 100. During delivery of fluid contents, plunger 200 moves axially through barrel 110 in the direction of the solid arrow shown in FIG. 9 until recessed seat 810 of plunger seal 800 has coupled with plunger-engaging member 421 of retractable needle body 420 to thereby couple needle body 420 and plunger member 210. Plunger 200 continues to move axially so that seal 800 continues to bear against needle seal 430. Needle seal 430 is incapable of axial movement relative to barrel adapter 300, so body 431 of needle seal 430 compresses sufficiently to allow arm 232 of control rod 230 to contact release ring 130 of collar 113 to thereby disengage ledge 235 of arm 232 from rim 229 of head 222 of plunger outer 220 which allows disengagement of control rod 230 from plunger outer 220 to facilitate decompression of spring 270 which serves to disengage (pull out) retaining step 423 of needle body 420 from needle retaining portion 436 of needle seal 430 for retraction of needle assembly 400 into barrel 110 of syringe 100. Fluid reclaim channels 427A,B in needle body 420 assist in channeling residual fluid into bore 424 and cannula 410. This minimizes "dead volume" and thereby improves the efficiency with which fluid contents of syringe 100 are delivered.

Figure 10:
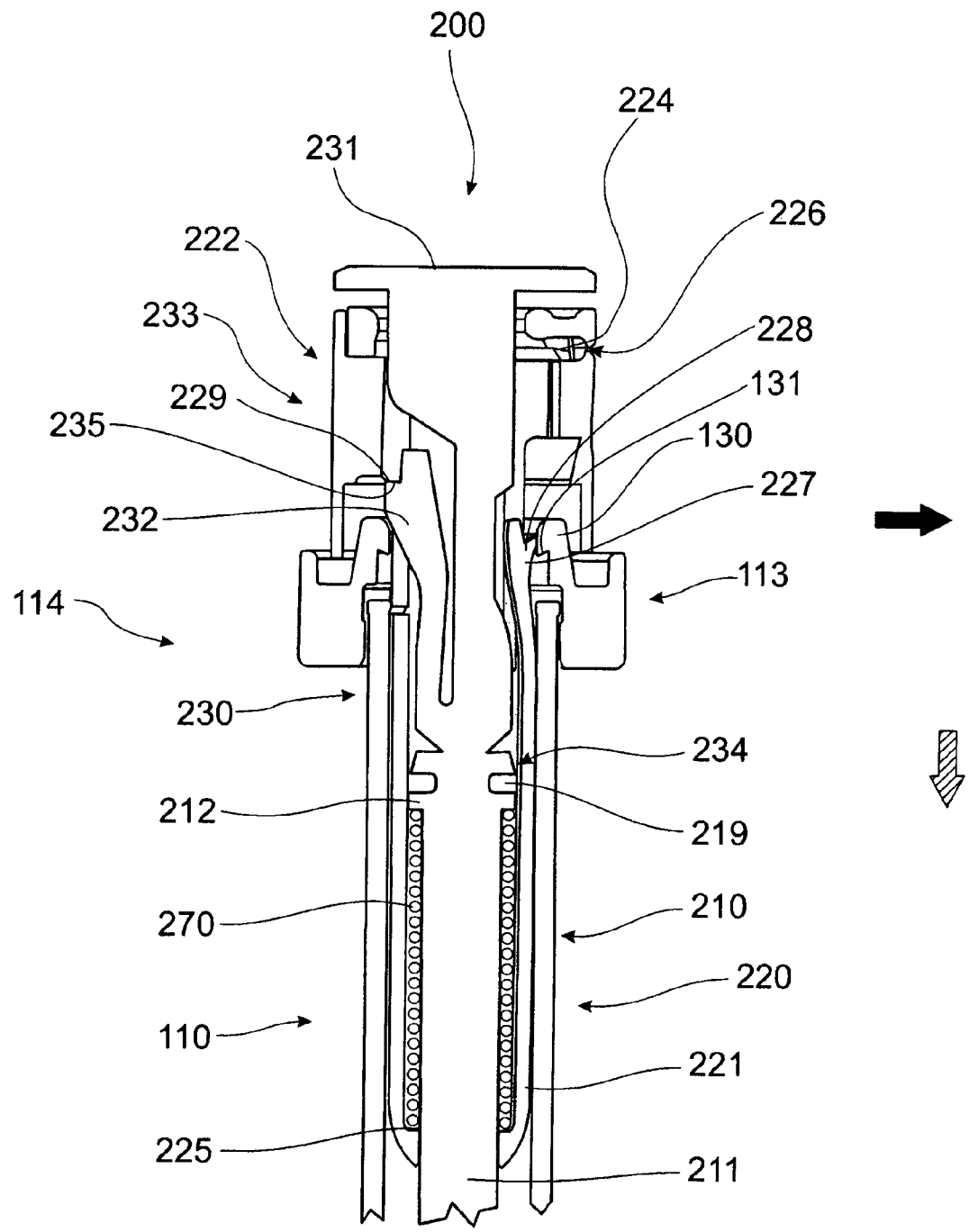
FIG. 10 is a sectional view of an embodiment of a plunger immediately before retraction.
Figure 11:
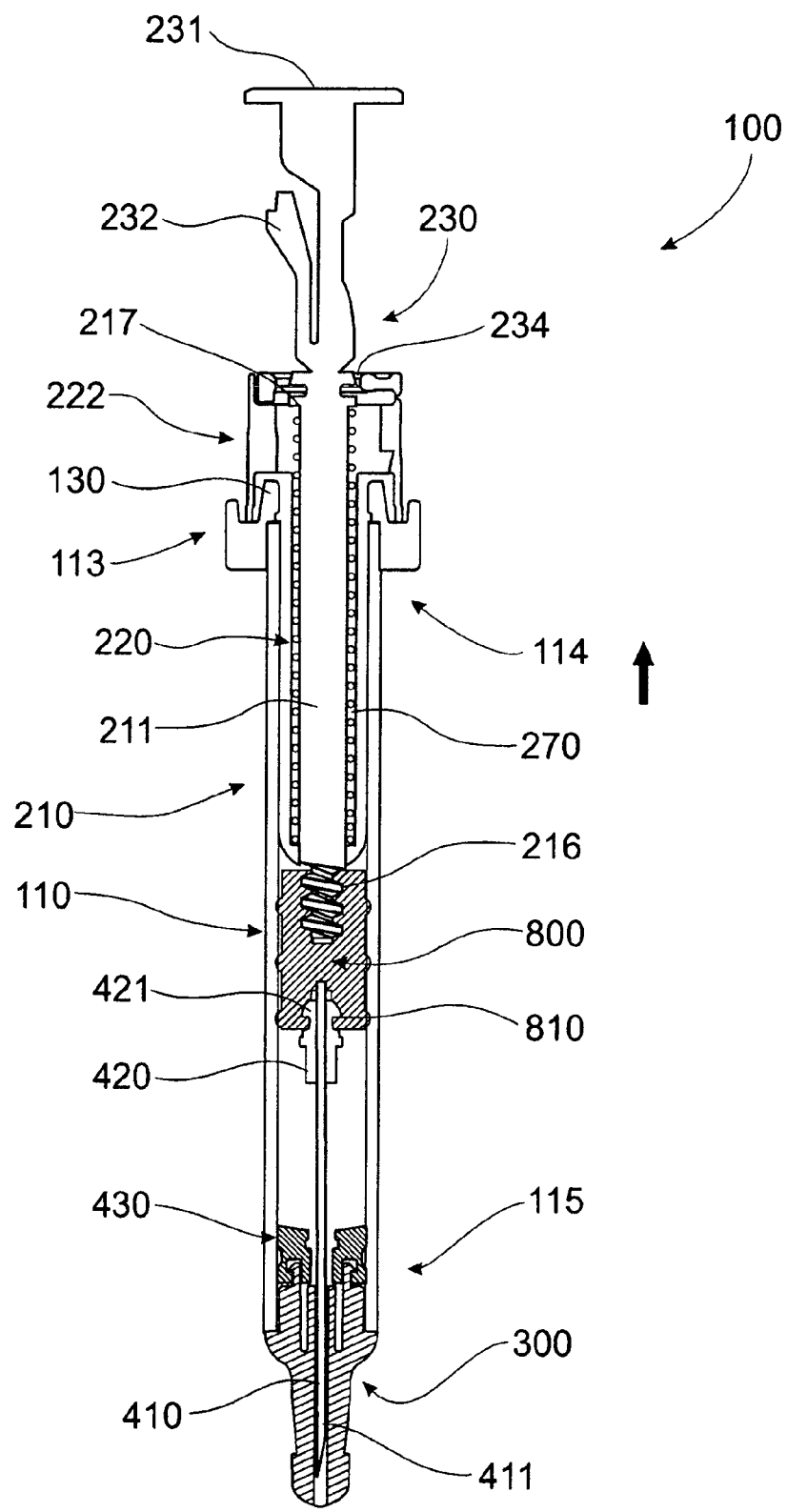
FIG. 11 is a sectional view of an embodiment of a retractable syringe during retraction of a plunger and retractable needle engaged therewith.

Referring to FIG. 10, at the end of injection of fluid contents, abutment 228 of locking finger 227 of plunger outer 220 engages underside 131 of release ring 130 to thereby prevent movement of plunger outer 220 out of barrel 110. In order for retractable needle body 420 and cannula 410 coupled to plunger member 210 to retract, compressed spring 270 must decompress, which is facilitated by plunger member 210 disengaging from plunger outer 220. Again referring to FIG. 10, arm 232 of control rod 230 bears against release ring 130 of collar 113 at plunger end 114 of barrel 110. Release ring 130 forces arm 232 to move radially inwardly in the direction of the horizontal solid arrow and out of engagement with rim 229 of head 222 of plunger outer 220 in FIG. 10. This disengagement allows compressed spring 270 to decompress and push against ledge 212 of plunger member 210 to thereby retract plunger member 210 with control rod 230 coupled thereto, as shown in FIG. 11. This disengagement may also be accompanied by an audible and/or tactile signal (e.g. a "click") which indicates to the user that retraction will occur. Needle body 420 is coupled to plunger seal 800 and so retracts (together with cannula 410) with plunger member 210 in the direction of the arrow in FIG. 11 inside barrel 110, thereby being completely: enveloped by, and contained within, barrel 110. While needle retraction is "automatically" driven by decompression of spring 270, the rate of retraction can be controlled by a user relaxing pressure (such as by way of thumb pressure) against button 231 of control rod 230.

Figure 12:
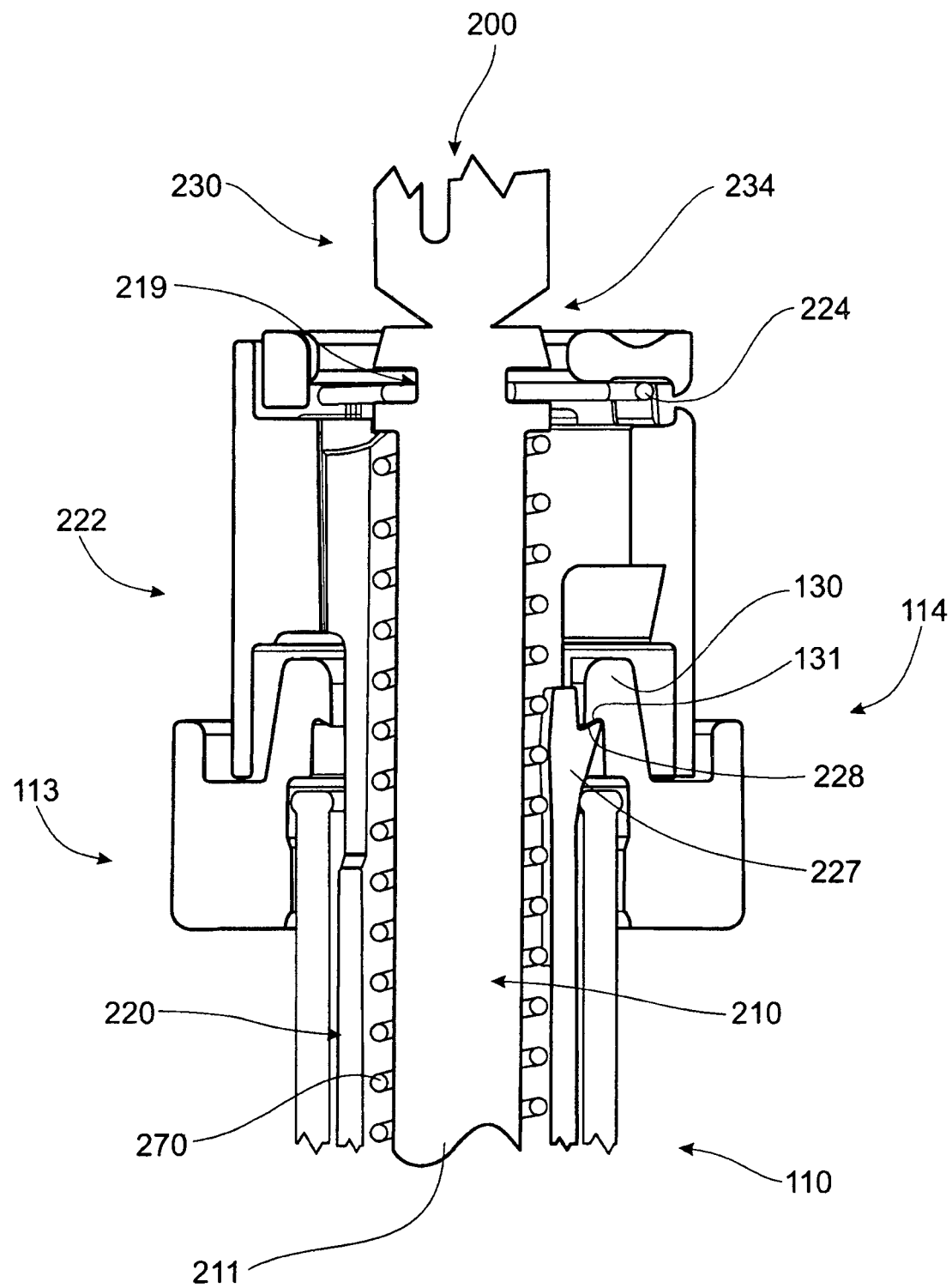
FIG. 12 is a sectional view of a lock formed between a barrel collar and a plunger outer after plunger retraction and a lock between a plunger outer and plunger inner.

Referring to FIG. 12, at the end of retraction of plunger member 210, further movement of plunger member 210 relative to plunger outer 220 and/or barrel 110 is prevented by lock spring 224 "snap locking" around locking groove 219 in plunger member 210. The locking of plunger member 210 at the end of retraction prevents inadvertent removal of plunger member 210 from plunger outer 220 and also prevents inadvertent depression of plunger member 210, both of which would expose cannula tip 411 and thereby expose the user to a potential needle stick injury.

At the end of retraction, control rod 230 can be broken from plunger member 210 at frangible junction 234 and manually removed from retractable syringe 100 and discarded as "clean" waste so that there is little if any plunger 220 protruding externally from plunger outer 220 with which to attempt to force plunger 200 back into barrel 110 and attempt to re-engage the needle (not shown).

Figure 13:
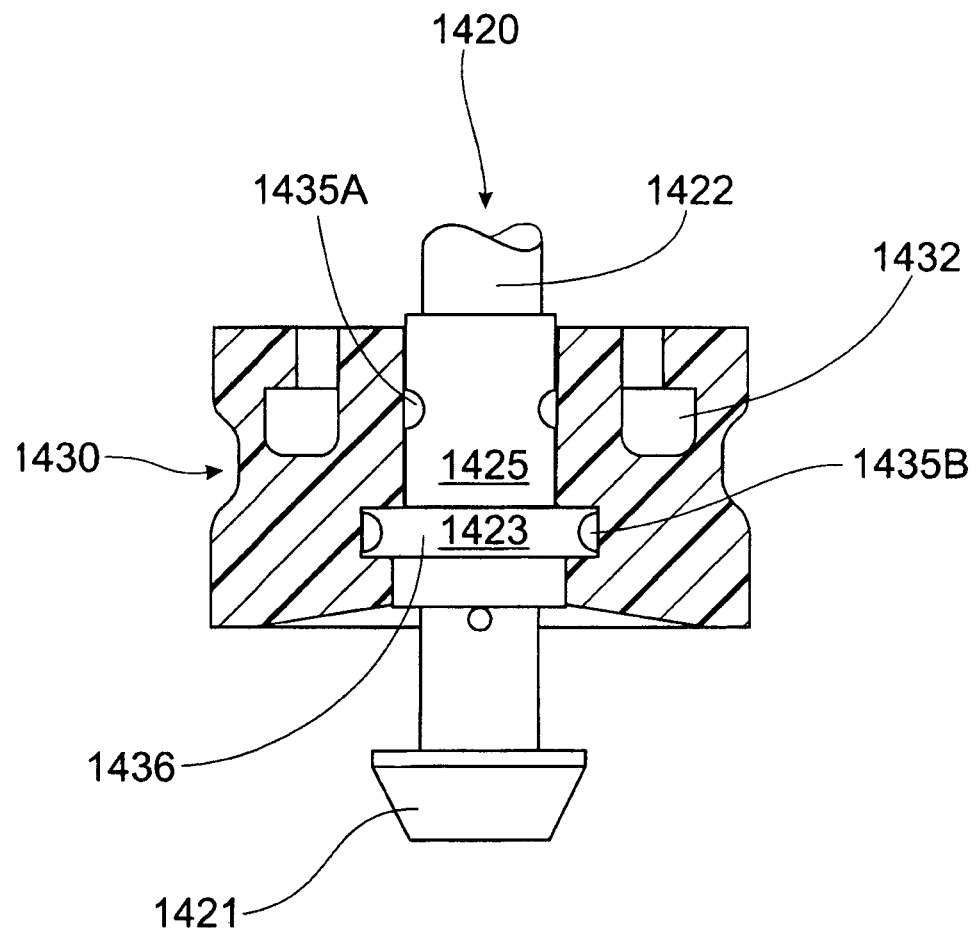
FIG. 13 is a sectional view of an alternative embodiment of a needle seal.

Referring now to FIG. 13 an alternative embodiment of needle seal 430 is described. In this embodiment, needle seal 1430 comprises one or more internal, circumferential ribs 1435A, B that respectively bear against neck 1423 and retaining step 1423 of needle body 1420. Internal, circumferential ribs 1435A, B contacting needle body 1420 may better resist "needle push" force and thereby retain needle body 1420 in place prior to retraction. One or a plurality of internal, circumferential ribs 1435 may be used to optimize a balance between needle retention and the force required to retract needle body 1420.

Figure 14:
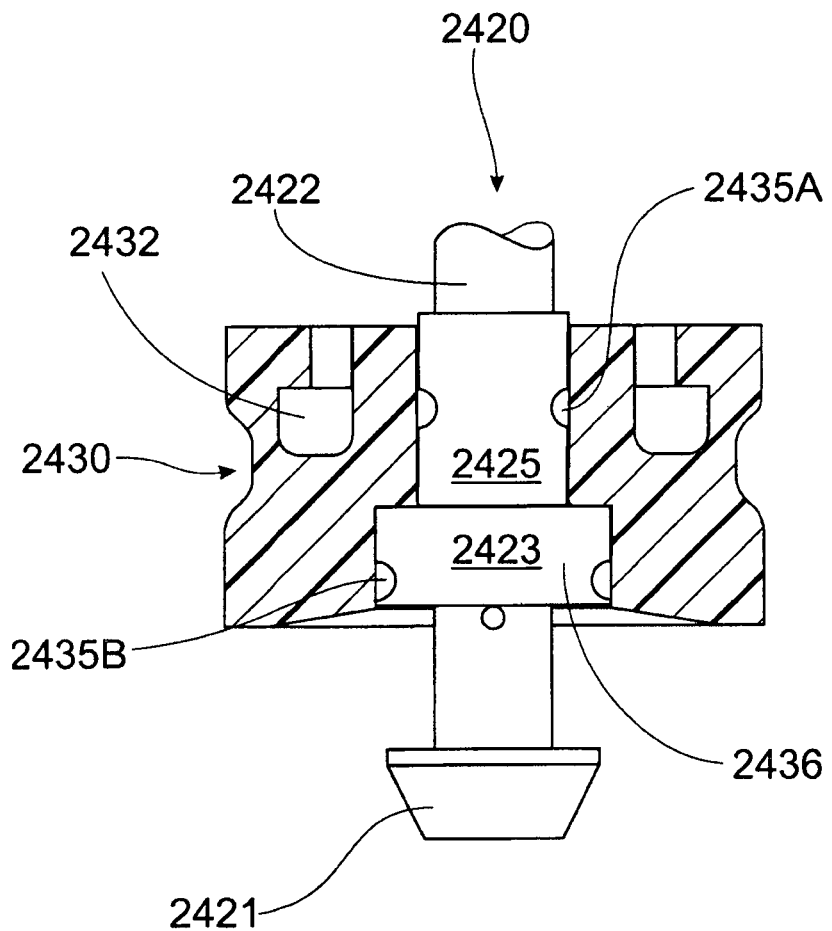
FIG. 14 is a sectional view of another alternative embodiment of a needle seal and an alternative embodiment of a needle body.

Referring now to FIG. 14, a similar embodiment of needle seal to that shown in FIG. 13 is described together with an alternative embodiment of needle body 420. Needle seal 2430 comprises one or more internal, circumferential ribs 2435A, B that respectively bear against neck 2425 and retaining step 2423 of needle body 2420. In this embodiment, the relative depth or axial length of retaining step 2423 and neck 2425 is reduced to a 2:1 ratio of neck 2425 to retaining step 2423, which is less than that of the embodiment shown in FIG. 13. The embodiment of FIG. 14 may better resist "needle push" force and thereby retain needle body 2420 in place prior to retraction. It will be appreciated that the relative depth or axial length of retaining step 2423 and neck 2425 may be varied to optimize a balance between needle retention and the force required to retract needle body 2420.

Figure 15:
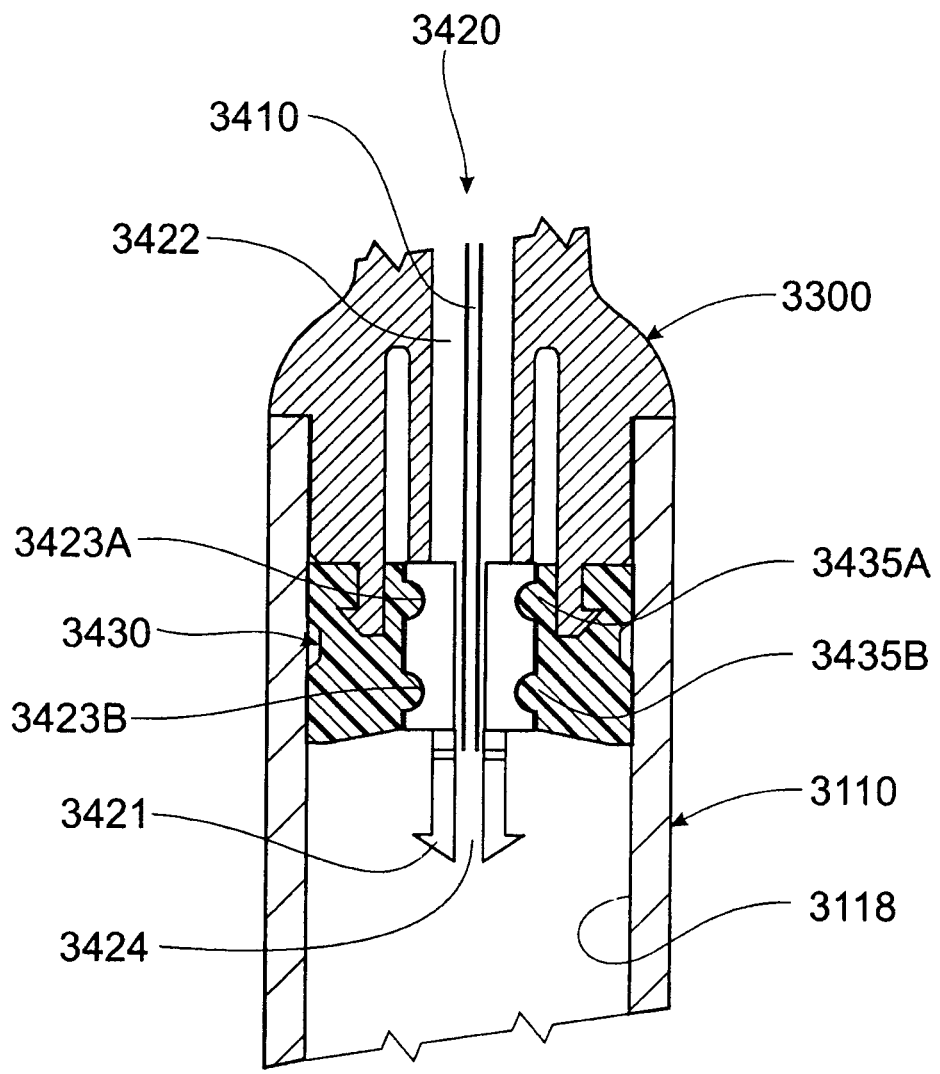
FIG. 15 is a sectional view of yet another alternative embodiment of a needle seal and needle body.

Yet another embodiment is shown in FIG. 15 where needle seal 3430 comprises one or more internal, circumferential ribs or rings 3435A, B that respectively bear against complementary annular recesses 3423A, 3423B of needle body 3420. In this embodiment, the coupling between circumferential ribs or rings 3435A, B and annular recesses 3423A, 3423B adopts an overall "hourglass" shape. It is anticipated that this coupling will provide sufficiently strong coupling to resist a 6 Newton "push" force while enabling needle body 3420 to be retractable from needle seal 3430 at the appropriate time.

In light of the foregoing it will be appreciated that the present invention provides a relatively simple, robust and inexpensive syringe that is automatically disabled with little or no assistance from the user to thereby prevent, or at least minimize the likelihood of, re-use of the syringe and/or needlestick injury by a used syringe.

More particularly, the barrel adapter allows the needle assembly to be mounted to any straight-barrel or substantially cylindrical barrel without the need for a specially manufactured barrel to fit the needle assembly.

Furthermore, the needle assembly and retraction system is simplified by eliminating the need for a separate ejector to assist release of the needle to facilitate retraction.

Reference is also made to the dual locking systems described herein whereby the plunger outer is locked to the barrel and the plunger member is locked to the plunger outer to thereby prevent removal and/or further movement of the plunger. In particular, the lock spring can resist up to 100 Newtons force to prevent or impede further movement of the plunger member after retraction. By providing dual locking systems, inadvertent failure of one or the other locking systems, or overcoming one or the other locking systems through tampering by an illicit user, does not result in the complete failure of plunger lockout.

It will also be appreciated that the fluid reclaim channels in the retractable needle body provide more efficient delivery of fluid contents timed to occur just before retraction of the needle. In cases where the fluid contents are an expensive drug or other compound, on a mass produced scale this improved efficiency can result in considerable cost savings.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

The invention claimed is:

1. A needle assembly and an adapter mountable to a substantially cylindrical retractable syringe barrel, the needle assembly comprising a needle body, a cannula and a needle seal adapted to seal against an inside wall of the substantially cylindrical retractable syringe barrel, the needle body and needle seal being releasably engaged, said adapter comprising a body that includes a needle portion comprising a spigot configured to releasably engage the needle body of the needle assembly mounted to the adapter, a barrel-engaging portion, and at least one barb, the needle seal including one or more members adapted to receive the at least one barb to couple the adapter to the needle seal which releasably engages the needle body of the needle assembly.

2. The needle assembly and the adapter of claim 1, wherein the adapter further comprises a needle aperture through which extends the cannula of the needle assembly.

3. The needle assembly and the adapter of claim 1 wherein the one or more members include a barb seat.

4. The needle assembly and the adapter of claim 1, wherein the barrel-engaging portion comprises a circumferential shoulder mountable to a rim at a needle end of said substantially cylindrical barrel.

5. The needle assembly and the adapter of claim 1, whereby in use the needle seal is substantially immobile during retraction of said needle body and cannula.

6. The needle assembly and the adapter of claim 1, wherein the needle seal is compressible.

7. The needle assembly and the adapter of claim 1, wherein the needle body comprises a plunger-engaging portion.

8. The needle assembly and the adapter of claim 1, which does not include an ejector member.

9. The needle assembly and the adapter of claim 1, which does not include a retaining member separate to the needle seal.

10. The needle assembly and the adapter of claim 1, wherein the needle body comprises one or more fluid reclaim channels.

11. A substantially cylindrical retractable syringe barrel comprising the needle assembly and the adapter of claim 1 mounted thereto.

12. A retractable syringe comprising the substantially cylindrical retractable syringe barrel of claim 11 and a plunger.

13. The retractable syringe of claim 12, wherein the plunger comprises a plunger member, a plunger outer and a biasing member, wherein the plunger member and plunger outer co-operate to releasably maintain said biasing member in an initially energized state before needle retraction.

* * * * *